(12) United States Patent
Kim et al.

(10) Patent No.: US 8,168,197 B2
(45) Date of Patent: May 1, 2012

(54) **EXTERNAL COMPOSITION FOR SKIN CONTAINING *SCROPHULARIA BUERGERIANA* MIQ. EXTRACT AND THE USE THEREOF FOR THE SKIN MOISTURIZING COSMETICS**

(75) Inventors: Han Sung Kim, Seongnam-si (KR); Chan Woo Lee, Suwon-si (KR); Youn Joon Kim, Seoul (KR); Jee Eun Kim, Seoul (KR); Duck Hae Kim, Seoul (KR); Ih Seop Chang, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 12/528,774

(22) PCT Filed: Sep. 19, 2007

(86) PCT No.: PCT/KR2007/004556
§ 371 (c)(1),
(2), (4) Date: Oct. 9, 2009

(87) PCT Pub. No.: WO2008/105579
PCT Pub. Date: Sep. 4, 2008

(65) Prior Publication Data
US 2010/0068310 A1 Mar. 18, 2010

(30) Foreign Application Priority Data
Feb. 28, 2007 (KR) .................. 10-2007-0020263

(51) Int. Cl.
*A61K 36/00* (2006.01)

(52) U.S. Cl. .................. 424/195.15; 424/401; 424/725

(58) Field of Classification Search .................. None
See application file for complete search history.

(56) References Cited

U.S. PATENT DOCUMENTS 5,716,800 A 2/1998 Meybeck et al.

FOREIGN PATENT DOCUMENTS

| JP | 11-199463 A | | 7/1999 |
| JP | 2005-145891 A | | 6/2005 |
| KR | 2003-0079105 | * | 10/2003 |
| KR | 10-2004-0074696 A | | 8/2004 |
| KR | 10-2004-0074697 A | | 8/2004 |

OTHER PUBLICATIONS

English translation of JP 11-199463 (1999).*
English translation of JP 2005-145891 (2005).*
Chinese Patent Office, Office Action issued Jun. 15, 2011, in corresponding Chinese Patent Application No. 200780051804.2 (in the name of Amorepacific Corporation).

* cited by examiner

*Primary Examiner* — Susan Hoffman
(74) *Attorney, Agent, or Firm* — Sughrue Mion, PLLC (57) ABSTRACT

Disclosed herein is a skin external composition for alleviating dry skin symptoms, which contains an extract of *Scrophularia buergeriana* Miq. as a main component and further contains an extract of *Poria cocos* Wolf, as well as the use thereof for skin-moisturizing cosmetics. The composition contains, as active ingredients, the *Scrophularia buergeriana* Miq. extract and the *Poria cocos* Wolf extract, which are prepared by extracting each of *Scrophularia buergeriana* Miq. and *Poria cocos* Wolf using water, ethanol, methanol, hexane, ethyl acetate or butanol.

8 Claims, 4 Drawing Sheets

Skin water content after application with acetone

FIG. 6

Total ceramide amount

FIG. 7

EXTERNAL COMPOSITION FOR SKIN CONTAINING *SCROPHULARIA BUERGERIANA* MIQ. EXTRACT AND THE USE THEREOF FOR THE SKIN MOISTURIZING COSMETICS

CROSS REFERENCE TO RELATED APPLICATIONS

This application is a National Stage of International Application No. PCT/KR2007/004556 filed Sep. 19, 2007, claiming priority based on Korean Patent Application No. 10-2007-0020263 filed Feb. 28, 2007, the contents of all of which are incorporated herein by reference in their entirety.

TECHNICAL FIELD

The present invention relates to a skin external composition for alleviating dry skin symptoms, which contains an extract of *Scrophularia buergeriana* Miq. as a main component and further contains an extract of *Poria cocos* Wolf, as well as the use thereof for skin-moisturizing cosmetics. More specifically, the present invention related to a skin external composition comprising an extract of *Scrophularia buergeriana* Miq. and an extract of *Poria cocos* Wolf, which, when applied on the skin, can normally restore and maintain the differentiation of skin keratinocytes, and thus can prevent or alleviate dry skin symptoms, atopic symptoms and contact dermatitis, which occur due to incomplete epidermal differentiation, as well as the use thereof for skin-moisturizing cosmetics.

BACKGROUND ART

The most important functions of the epidermis that is the outermost layer of the skin are protective functions to protect the body from various external stimuli (physical and chemical stimuli, including chemical substances, pollutants, dry environments and UV rays) and to prevent the excessive evaporation of water in the body through the skin. Such protective functions can be maintained only when the stratum corneum (horny layer) consisting of keratinocytes is normally formed. The stratum corneum that is the outermost layer of the epidermis is formed from keratinocytes and consists of differentiated keratinocytes and lipids surrounding the keratinocyts (J. Invest. Dermatol. 1983; 80: 44-49). Keratinocytes are characteristic cells formed through a process in which basal cells continuously proliferating in the lowest layer of the epidermis undergo a stepwise change in the shape and function thereof and rise to the surface of the skin. After the passage of a given period of time, dead keratinocytes are removed from the skin and replaced with new keratinocytes, and such a repeated process is called the "differentiation or keratinization of epidermal cells". During the keratinization process, keratinocytes produce intracellular lipids (ceramide, cholesterol and fatty acid) with natural moisturizing factors (NMF) while forming the stratum corneum, such that the stratum corneum has firmness and flexibility to function as a skin barrier.

However, the stratum corneum easily loses its function due to living habitual factors, such as excessive washing or bathing, environmental factors, such as dry atmospheres or pollutants, and endogenous diseases, such as atopic skins or senile skins. In fact, persons suffering from dry skin symptoms due to various factors, and various disorders caused by the dry skin symptoms, have recently gradually increased. Thus, in order to maintain the skin water content at a suitable level, many studies focused on supplying water from an external source or on preventing the loss of water from the body have been conducted, and in fact, various kinds of moisturizers having water-holding capacity have been developed and mainly used in the cosmetic field.

However, as environmental factors harmful to the human body gradually increase and the aged population increases rapidly, persons having skin conditions, in which the turnover rate of the stratum corneum decreases, the lipid synthesizing ability of keratinocytes decreases, or the normal division, growth and differentiation of cells in the epidermis do not become smooth, so that the amount of moisturizing factors and lipids in the stratum corneum is reduced, and thus the normal function of the stratum corneum is not maintained, that is, the skin barrier function is impaired, are gradually increasing.

Such abnormal division and differentiation of epidermal cells result in various skin diseases, including dry skin (xerosis), atopy and psoriasis. When moisturizers having a water-holding function in themselves are used, such skin diseases can be slightly alleviated, but it is difficult to expect the fundamental treatment of the skin diseases.

DISCLOSURE

Technical Problem

Accordingly, the present inventors have developed a substance regulating the differentiation of epidermal cells and have attempted the developed substance on the skin to induce the normal production and removal of the stratum corneum and enhance the production and maintenance of natural moisturizing factors in the stratum corneum of the skin so as to fundamentally prevent or treat dry skin diseases, including dry skin (xerosis) and atopy caused thereby.

The present inventors have conducted studies associated with the differentiation of epidermal cells and, as a result, have found that an extract of *Scrophularia buergeriana* Miq. and an extract of *Poria cocos* Wolf function to promote the differentiation of keratinocytes and, in addition, promote the synthesis of the intracellular lipid ceramide and activate peroxisome proliferator activated receptor-alpha (PPAR-$\alpha$), a kind of nuclear hormone receptor, which promotes the differentiation of keratinocytes, inhibits the proliferation of keratinocytes, increases the synthesis of intracellular lipids, and through such findings, the present inventors could further confirm the effects of the *Scrophularia buergeriana* Miq. extract and the *Poria cocos* Wolf extract. Also, the present inventors have found that, when the extracts are applied to the animal skin in the form of a skin external preparation, they enhance the skin barrier function, thereby completing the present invention.

Therefore, it is an object of the present invention to promote the normal differentiation of keratinocytes in the epidermis to induce the following effects: (1) the effect of normally inducing keratinocytes, which are backbone components forming the stratum corneum and the skin barrier, such that the skin can be protected from external physical stimuli; and (2) the effect of promoting the biosynthesis of lipids, which surround keratinocytes to form the skin barrier, such that the skin barrier can be enhanced. Another object of the present invention is to provide an external composition for skin moisturization, which can increase the water-holding capacity of the skin through the effects of the extracts to increase the flexibility and firmness of the skin, thus allowing the skin to smoothly perform the original protective function thereof, and, in addition, can reduce the formation of fine wrinkles caused by skin drying, thus prevent or treat dry skin diseases, such as dry skin or atopy.

TECHNICAL SOLUTION

To achieve the above objects, the present invention provides an external composition for skin moisturization, which contains an extract of *Scrophularia buergeriana* Miq. as an active ingredient.

The composition according to the present invention may further contain, in addition to the *Scrophularia buergeriana* Miq. extract, an extract of *Poria cocos* Wolf.

The external composition for skin moisturization preferably contains 0.0001-30 wt % of the *Scrophularia buergeriana* Miq. extract.

Also, the external composition for skin moisturization is preferably used to enhance the skin barrier function, promote the differentiation of keratinocytes, promote the production of ceramide or activate PPAR-α.

In addition, the present invention provides the use of the external composition, containing the *Scrophularia buergeriana* Miq. extract as an active ingredient, for skin-moisturizing cosmetics.

Hereinafter, the present invention will be described in detail.

*Scrophularia buergeriana* Miq., which is used in the present invention, is a perennial plant belonging to the family Scrophulariaceae, and is distributed in Korea, China, Japan, etc., and the root thereof is used as a medicinal material in Chinese medicine. It contains, as main components, scrophularine, phytosterol and phytosterine and, in addition, contains saccharides, essential oils, fatty acids, etc. *Scrophularia buergeriana* Miq. has the effects of lowering fever and improving cardiac functions, and thus it is used for sore throat, tonsillitis, conjunctivitis, lymphadenitis and the like and is effective against various diseases with fever.

*Poria cocos* Wolf, which is used in the present invention, is a member of the family Polyporaceae and lives on the root of pine trees. It is in the form of a fungal mass having a diameter of about 30-50 cm, the outside thereof is rough like the pine tree bark, and the inside thereof is white or pink in color. *Poria cocos* Wolf, the inside of which is white in color, lives on the root of pine trees, and *Poria cocos* Wolf, the inside of which is pink in color, lives on the root of Japanese pine tree. The triterpene component of *Poria cocos* Wolf was reported to have anti-vomiting and anti-inflammatory effects, etc., and the sclerotium of *Poria cocos* Wolf contains β-pachyman in an amount corresponding to about 93% of the dry weight of *Poria cocos* Wolf. It also contains triterpenoid compounds, pachymic acid, tumulosic acid, 3β-hydroxylanosta-7,9 and 24-triene-2-acid and, in addition, contains chitin, sterol, lecithin, adenine, histidine, choline, lipase, proteinase, etc. Also, *Poria cocos* Wolf has been used as a tonic for a long time. The results of pharmacological tests revealed that *Poria cocos* Wolf has a diuretic effect, a blood glucose-lowering effect and a sedative effect, and it is known to have an immune-activating effect. Also, it is known to be effective for women's diseases.

In the external composition for skin moisturization according to the present invention, the *Scrophularia buergeriana* Miq. extract or the combination of the *Scrophularia buergeriana* Miq. extract and the *Poria cocos* Wolf extract is preferably contained in an amount of 0.0001-30 wt % based on the total weight of the composition. If the content of the extract is less than 0.0001 wt %, the extract cannot provide the skin-moisturizing effect, the effect of enhancing the skin barrier function, and the effect of inducing the differentiation of skin keratinocytes, and if the content exceeds 30 wt %, the increase in the content will not lead to a significant increase in the effect of the extract.

The external composition for skin moisturization according to the present invention can be provided as a cosmetic composition or a pharmaceutical composition, and the formulation of the inventive composition will now be described in further detail.

The cosmetic composition according to the present invention may contain, in addition to the above-described *Scrophularia buergeriana* Miq. extract and *Poria cocos* Wolf extract, other components, which can increase the main effects of the present invention, as long as the main effects of the present invention are not adversely affected.

Although the above-described *Scrophularia buergeriana* Miq. extract and *Poria cocos* Wolf extract of the present invention are preferably formulated into cosmetic preparations and applied on the skin, they may also be prepared in the form of conventional external preparations.

A cosmetic composition containing the inventive composition containing the above-described *Scrophularia buergeriana* Miq. extract and *Poria cocos* Wolf extract may be in the form of a solution, an emulsion or a viscous mixture.

The cosmetic composition of the present invention can be used in various cosmetics in order to provide the effect of moisturizing the skin, the effect of enhancing the skin barrier function or the effect of inducing the differentiation of skin keratinocytes. Examples of products, to which the composition of the present invention, include cosmetics, such as creams, lotions and skin lotions, cleansing foams, face cleansers, soaps, beauty solutions, etc.

Specifically, there is no particular limitation on the formulation of the cosmetic composition of the present invention, and examples of the formulation of the cosmetic composition may include skin lotion, astringent lotion, milk lotion, nourishing cream, massage cream, essence, eye cream, eye essence, pack, gel, powder, makeup base, foundation, ointment, patch, beauty solution, cleansing foam, cleansing cream, cleansing water, body lotion, body cream, body oil, body essence, shampoo, rinse, body cleanser, soap, hair dye, spray and the like.

In a cosmetic composition having each formulation, other components in addition to the above-described *Scrophularia buergeriana* Miq. extract and *Poria cocos* Wolf extract can be suitably selected without difficulty by those skilled in the art depending on the formulation or intended use of the cosmetic composition.

The pharmaceutical composition according to the present invention may further contain suitable carriers, excipients or diluents, which are conventionally used in the preparation of pharmaceutical compositions.

The inventive pharmaceutical composition containing the above-described *Scrophularia buergeriana* Miq. extract and *Poria cocos* Wolf extract can be formulated into various preparations suitable for pharmaceutical application, including external preparations, such as ointments, gels, creams, patches or sprays, according to conventional methods. Each of such preparations may contain various bases and additives, which are required and suitable for the formulation thereof, and the kinds and amounts of these components can be easily selected by those skilled in the art.

The dose of each of the preparations varies depending on the age, sex, weight and disease condition of a patient and the mode of administration, but each of the preparations is preferably applied at a dose of 1.0-3.0 ml/day 1-5 times a day for at least one month.

Meanwhile, the *Scrophularia buergeriana* Miq. extract and *Poria cocos* Wolf extract of the present invention have little or no toxicity and side effects, and thus can be safely used for preventive purposes for a long period of time.

ADVANTAGEOUS EFFECTS

The external composition for skin moisturization according to the present invention is characterized in that it contains, in addition to the *Scrophularia buergeriana* Miq. extract, the *Poria cocos* Wolf extract. The skin external composition of the present invention can normally induce keratinocytes, which are backbone components forming the stratum corneum and the skin barrier, such that the skin can be protected from external physical stimuli. Also, the external composition of the present invention can promote the biosynthesis of lipids, which surround keratinocytes to form the skin barrier, such that the skin barrier can be enhanced. By virtue of such effects, the inventive skin external composition containing said *Scrophularia buergeriana* Miq. extract and *Poria cocos* Wolf extract can be advantageously used as a cosmetic or pharmaceutical composition for skin moisturization in order to prevent or alleviate dry skin, atpoic dermatitis, contact dermatitis or psoriasis, which occur due to the incomplete differentiation of the epidermis, and to enhance the skin barrier function and induce the differentiation of skin keratinocytes.

MODE FOR INVENTION

Hereinafter, the present invention will be described in further detail with reference to examples and test examples, but the scope of the present invention are not limited only to these examples.

As described in Reference Examples 1 to 6 of the present invention, a *Scrophularia buergeriana* Miq. extract and a *Poria cocos* Wolf extract were prepared by extracting effective components from each of freeze-dried *Scrophularia buergeriana* Miq. and *Poria cocos* Wolf using each of extraction solvents and concentrating and drying the extracts.

Water, lower alcohol, such as methanol or ethanol, ethyl acetate or n-hexane, was added to *Scrophularia buergeriana* Miq. in an amount of 1-15 times the weight of the *Scrophularia buergeriana* Miq. Then, the *Scrophularia buergeriana* Miq. was extracted by heating at 50-100° C. for 3-24 hours or immersed in the solvent at 4-25° C. for 3-4 days to extract effective components therefrom. Also, the anhydrous or hydrated ethanol and methanol extracts were dissolved in a suitable amount of a mixed solvent of water with ethyl acetate, butanol or hexane and left to stand to separate it into layers, and then the upper layer was separated. The extracts thus obtained were concentrated using a vacuum evaporator and dried, and the dried extracts were dissolved in a solvent, such as water, ethanol or 1,3-butyleneglycol.

Dried powdery *Poria cocos* Wolf was also extracted in the same manner as in the above-described method for extracting *Scrophularia buergeriana* Miq. Specifically, water, lower alcohol, such as methanol or ethanol, ethyl acetate or n-hexane, was added to dried powdery *Poria cocos* Wolf in an amount of 1-15 times the weight of the *Poria cocos* Wolf, and the added *Poria cocos* Wolf was extracted by heating at 50-100° C. for 3-24 ours or immersed in the solvent at 4-25° C. for 3-4 to extract effective components therefrom. Also, the anhydrous or hydrated ethanol and methanol extracts were dissolved in a suitable amount of a mixed solvent of water with ethyl acetate, butanol or hexane and left to stand to separate it into layers, and then the upper layer was separated. The extracts thus obtained were concentrated using a vacuum evaporator and dried, and the dried extracts were dissolved in a solvent, such as water, ethanol or 1,3-butyleneglycol.

Because the extract obtained through the extraction method of Reference Example 1 among Reference Examples below had the highest effect, only the extract of Reference Example 1 will be mentioned in the following test examples for verifying the effects of the *Scrophularia buergeriana* Miq. extract and *Poria cocos* Wolf extract of the present invention. In addition, the effects of the extracts of Reference Examples 2 to 6 were generally lower than the extract of Reference Example 1 by about 10-50%, the scope of the present invention encompasses all the extracts of Reference Examples 1 to 6.

REFERENCE EXAMPLE 1

Preparation of Water Extracts of Herbal Medicinal Materials 200 g of each of freeze-dried *Scrophularia buergeriana* Miq. and *Poria cocos* Wolf (purchased from Kunwha Pharmaceutical Co., Ltd., Korea) was crushed, and a 10-fold weight of water was added thereto. Then, the herbal materials was extracted at 80° C. for 18 hours with sufficient stirring. The extracts were cooled to room temperature and filtered through filter paper, and each of the filtrates was added to 4 kg of ethanol and left to stand for 48 hours. Then, the solutions were filtered, and each of the formed precipitates was dissolved in 2 kg of distilled water and then filtered again. The resulting filtrate was concentrated in a vacuum evaporator, thus obtaining water extracts of *Scrophularia buergeriana* Miq. and *Poria cocos* Wolf.

REFERENCE EXAMPLE 2

Preparation of Ethanol Extracts of Herbal Medicinal Materials 200 g of each of freeze-dried *Scrophularia buergeriana* Miq. and *Poria cocos* Wolf was added to a 10-fold weight of 70% ethanol and heated at 80° C. for 2 hours to extract effective components therefrom. The extracts were left to stand at room temperature for 2 days to precipitate impurities, and were then filtered through filter paper twice. The filtrates were concentrated in a vacuum evaporator, thus obtaining ethanol extracts of *Scrophularia buergeriana* Miq. and *Poria cocos* Wolf.

REFERENCE EXAMPLE 3

Preparation of Methanol Extracts of Herbal Medicinal Materials 200 g of each of freeze-dried *Scrophularia buergeriana* Miq. and *Poria cocos* Wolf was added to a 10-fold weight of methanol and heated at 70° C. for 2 hours to extract effective components therefrom. The extracts were left to stand at room temperature for 2 days to precipitate impurities, and were then filtered through filter paper twice. The filtrates were concentrated in a vacuum evaporator, thus obtaining methanol extracts of *Scrophularia buergeriana* Miq. and *Poria cocos* Wolf.

REFERENCE EXAMPLE 4

Hexane and Ethylacetate Fractions of Herbal Medicinal Materials

Each of the *Scrophularia buergeriana* Miq. and *Poria cocos* Wolf extracts, prepared in Reference Example 3, was added to and completely suspended in a 20-fold weight of a mixed solvent of water and hexane (1:1). Then, each of the suspensions was left to stand at room temperature for 1 day to separate it into layers. Only the upper hexane layer was separated and concentrated in a vacuum evaporator, thus obtaining a hexane fraction of each of the *Scrophularia buergeriana* Miq. and *Poria cocos* Wolf extracts.

The lower water layer was added to and shaken in a 2-fold weight of an ethyl acetate solvent and was then left to stand at room temperature for one day to separate it into layers. The upper ethylacetate layer was separated and concentrated in a vacuum evaporator, thus obtaining an ethylacetate fraction of each of the *Scrophularia buergeriana* Miq. and *Poria cocos* Wolf extracts.

REFERENCE EXAMPLE 5

Butanol Fractions of Herbal Medicinal Materials

The lower water layer, obtained in the process of obtaining the ethylacetate fraction in Reference Example 4, was added to a 2-fold weight of butanol and treated in the same manner as in Reference Example 4, thus obtaining a butanol fraction of each of the extracts.

REFERENCE EXAMPLE 6

Water Fractions of Herbal Medicinal Materials

Each of the water layers, obtained in Reference Example 5, was concentrated in a vacuum evaporator, thus obtaining a water fraction of each of the *Scrophularia buergeriana* Miq. and *Poria cocos* Wolf extracts.

Each of the *Scrophularia buergeriana* Miq. and *Poria cocos* Wolf extracts or each of the concentrated *Scrophularia buergeriana* Miq. and *Poria cocos* Wolf extracts was dissolved in water at a concentration of 30% (w/w), 1,3-butyleneglycol at a concentration at a concentration of 5% (w/w) or ethanol at a concentration of 10% (w/w). Each of the solutions was added to cosmetic formulations, such as skin lotion, milk lotion, essence or pack.

In order to demonstrate the effects of the *Scrophularia buergeriana* Miq. and *Poria cocos* Wolf extracts, obtained in Reference Example 1 of the present invention, the following test was carried out. In Example 3 below, the *Scrophularia buergeriana* Miq. extract and the *Poria cocos* Wolf extract were mixed with each other at a ratio of 1:1.

TABLE 1

| | Examples | | |
|---|---|---|---|
| Components | 1 | 2 | 3 |
| *Scrophularia buergeriana* Miq. | ○ | | ○ |
| *Poria cocos* Wolf | | ○ | ○ |

TEST EXAMPLE 1

Induction of Differentiation of Human Keratinocytes

In order to examine the cell differentiation-promoting effects of the *Scrophularia buergeriana* Miq. and *Poria cocos* Wolf extracts, tests were carried out using the following two methods: (1) a method of measuring the amount of cornified envelops (CE), formed in the differentiation of keratinocytes, using absorbance; and (2) a method of measuring the amount of cornified envelops (CE), formed in the differentiation of keratinocytes, using an isotope.

Figure 1:
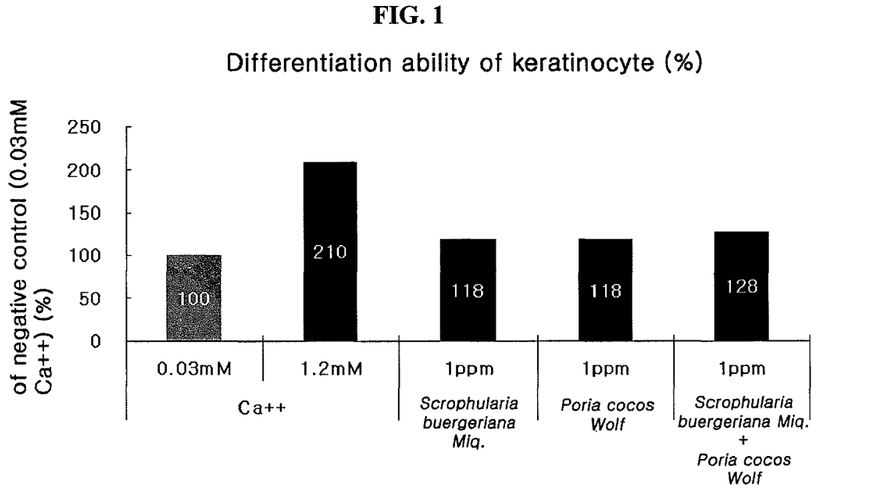
FIG. 1 depicts the differentiation ability of keratinocytes treated with *Scrophularia buergeriana* Miq. extract alone, *Poria cocos* Wolf extract alone, or a combination of the two extracts, versus $Ca^{2+}$ controls.

In the first test of measuring absorbance, primarily cultured human keratinocytes were placed in a culture flask and allowed to adhere to the flask bottom. Then, the test materials shown in Table 2 below were added to the culture media at the concentrations shown in Table 2, and the cells were cultured for 5 days, until the cells reached a confluence of about 70-80%. The cells were harvested and washed with phosphate buffered saline (PBS). Then, 1 ml of 10 mM of Tris-HCl (pH 7.4), containing 2% sodium dodecyl sulfate (SDS) and 20 mM dithiothreitol (DTT), was added to the cells, which were then sonicated, boiled and centrifuged. The centrifuged precipitate was suspended again in 1 ml of PBS and measured for absorbance at 340 nm. Meanwhile, a portion of the solution after the sonication was sampled, and the protein content thereof was measured and used as a reference in the evaluation of cell differentiation. A group treated with low calcium (0.03 mM) and a group treated with high calcium (1.2 mM) were used as a negative control group and a positive control group, respectively, and the results of the test performed by adding the test materials to a low concentration of calcium are shown in Table 2 and FIG. 1.

Figure 2:
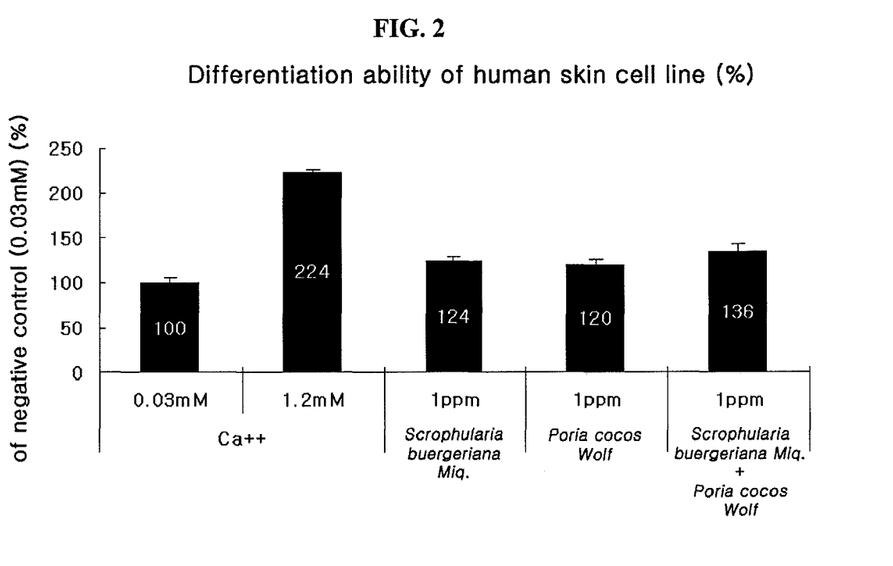
FIG. 2 depicts the differentiation ability of human skin cells treated with *Scrophularia buergeriana* Miq. extract alone, *Poria cocos* Wolf extract alone, or a combination of the two extracts, versus $Ca^{2+}$ controls.

In the second test of measuring the amount of cornified envelops using an isotope, a primarily cultured human skin cell line was placed in a 24-well culture flask and allowed to adhere to the flask bottom. Then, 1 uCi/ml of [35S]-methionine together with the test materials shown in Table 2 was added to the culture medium at the concentrations shown in Table 2, and the cells were cultured for 2 days, until the cells reached a confluence of about 70-80%. The cells were harvested and washed with PBS (phosphate buffered saline), and then 500 μl of PBS, containing 2% SDS (sodium dodecyl sulfate) and 20 mM DTT (dithiothreitol), was added thereto, and the cell solution was pipetted. Then, 100 μl of the cell solution was dispensed into each scintillation vial, 2.5 ml of a cocktail solution was added thereto, and the radioactivity of the cell solution was measured with a liquid scintillation counter (LSC) to determine the total protein amount. Based on the determined total protein amount, the corresponding amount of each of the test materials was filtered through a 25-mm filter. Only the insoluble protein remaining on the filter was taken, and the filter itself was placed in a scintillation vial. 2.5 ml of a cocktail solution was added thereto, the filter was well dissolved, and the radioactivity of the solution was measured with a liquid scintillation counter. The measured value was divided by the above-prepared total protein amount to determine the amount of CE formed in differentiation. The measurement results are shown in Table 2 below and FIG. 2.

TABLE 2

| Test material (water extract of Scrophularia buergeriana Miq.) | | Differentiation ability (%) of keratinocytes | Differentiation ability (%) of human skin cell line |
|---|---|---|---|
| Control groups | Low $Ca^{2+}$ (0.03 mM) | 100 | 100 |
| | High $Ca^{2+}$ (1.2 mM) | 210 | 224 |
| Groups treated with test material | 1.0 ppm Scrophularia buergeriana Miq. | 118 | 124 |
| | 1.0 ppm Poria cocos Wolf | 118 | 120 |
| | 1.0 ppm Scrophularia buergeriana Miq./Poria cocos Wolf mixture | 128 | 136 |

As can be seen in Table 2 above, the *Scrophularia buergeriana* Miq. and *Poria cocos* Wolf extracts according to the present invention promoted the differentiation of both the keratinocytes and the human skin cell line. Also, it could be observed that the use of the mixture of the *Scrophularia buergeriana* Miq. extract and the *Poria cocos* Wolf extract was more effective than the use of the *Scrophularia buergeriana* Miq. extract alone.

TEST EXAMPLE 2

Expression of Transglutaminase in Human Skin Cell Line

The human skin cell line was placed in each well of a 96-well cell culture plate at a concentration of $5\times10^4$ cells/well and allowed to adhere to the bottom for 24 hours. The adhered cell line was treated with ach of the test materials, and after 2 days, the media were removed, and the cells were stored in a refrigerator at −20° C. The cells were disrupted by repeating freezing-thawing twice, and then treated with a mixture of acetone:ethanol=1:1 (v/v) and left to stand at 4° C. for 30 minutes to immobilize the cells. The, the cells were left to stand to evaporate the organic solvent and were blocked using 1% fetal bovine albumin, transglutaminase (primary antibody) and HRP (horseradish peroxidase) anti-mouse secondary antibody, and o-phenyldiamine (OPD) was added to develop the color of the cells. The expression level of transglutaminase in the cells was determined by measuring absorbance at 490 nm, and the correction of the measurement was carried out by measuring the background at 630 nm. A group treated with low calcium (0.03 mM) and a group treated with high calcium (1.2 mM) were used as a negative control group and a positive control group, respectively, and the results of the test performed by adding the test materials to a low concentration of calcium are shown in Table 3 and FIG. 3.

TABLE 3

| Test material (water extract of Scrophularia buergeriana Miq.) | | Expression level (%) of transglutaminase |
|---|---|---|
| Control groups | Low $Ca^{2+}$ (0.03 mM) | 100 |
| | High $Ca^{2+}$ (1.2 mM) | 139 |
| Groups treated with test material | 1.0 ppm Scrophularia buergeriana Miq. | 260 |
| | 1.0 ppm Poria cocos Wolf | 210 |
| | 1.0 ppm Scrophularia buergeriana Miq./Poria cocos Wolf mixture | 268 |

Figure 3:
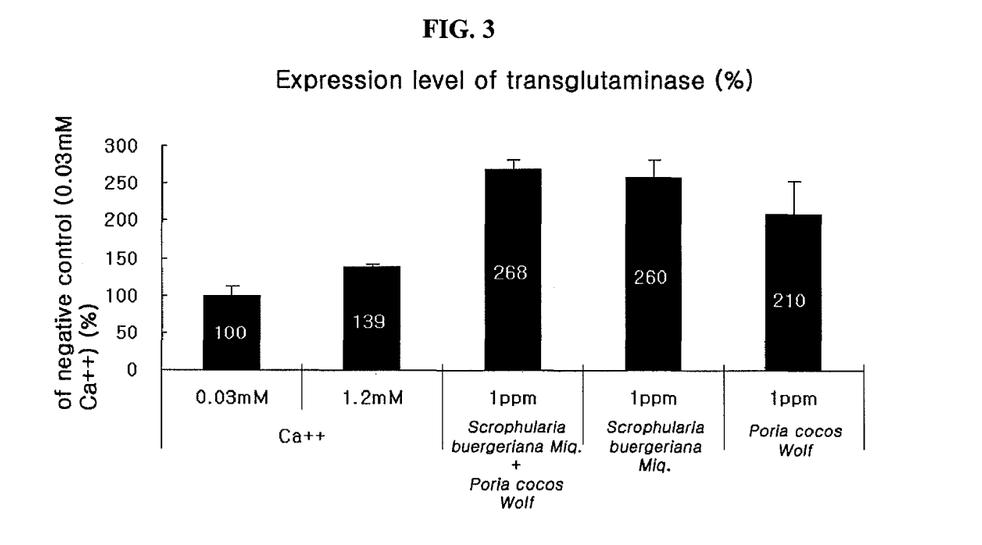
FIG. 3 depicts the expression level of transglutaminase in human skin cells treated with *Scrophularia buergeriana* Miq. extract alone, *Poria cocos* Wolf extract alone, or a combination of the two extracts, versus $Ca^{2+}$ controls.

As can be seen in Table 3 above and FIG. 3, the *Scrophularia buergeriana* Miq. and *Poria cocos* Wolf extracts according to the present invention showed an increase in transglutaminase expression level of more than two times that of the negative control group and showed a significant increase in transglutaminase expression level compared to the negative control group. Thus, it could be seen that the *Scrophularia buergeriana* Miq. and *Poria cocos* Wolf extracts according to the present invention increased the expression of transglutaminase. Also, it could be seen that the use of the mixture of the *Scrophularia buergeriana* Miq. extract and the *Poria cocos* Wolf extract was more, effective than the use of the *Scrophularia buergeriana* Miq. extract alone.

TEST EXAMPLE 3

Test of Skin Barrier Recovery and Moisturizing Capacity on Nude Mouse Skin

In order to evaluate the effects of the *Scrophularia buergeriana* Miq. and *Poria cocos* Wolf extracts on the recovery of skin barrier function impaired due to long-term skin injury, the following test was carried out. Acetone was applied on the back of 8-10-week-old nude mice twice a day for 5 days to impair the skin barrier function. Then, the transepidermal water loss (TEWL) of the mouse skin was measured with an evaporimeter, and only test animals having a skin showing a transepidermal water loss of more than 40 $g/m^2/hr$ was applied with each of a vehicle (propyleneglycol:ethanol=7:3) and a test material containing 5 wt % of the *Scrophularia buergeriana* Miq. extract/*Poria cocos* Wolf extract mixture, at a dose of 200 μl per 5 $cm^2$ of skin area twice a day for 3 days, while the TEWL of the mice skin was measured at a given time interval. The measurement results are shown in FIG. 4.

Figure 4:
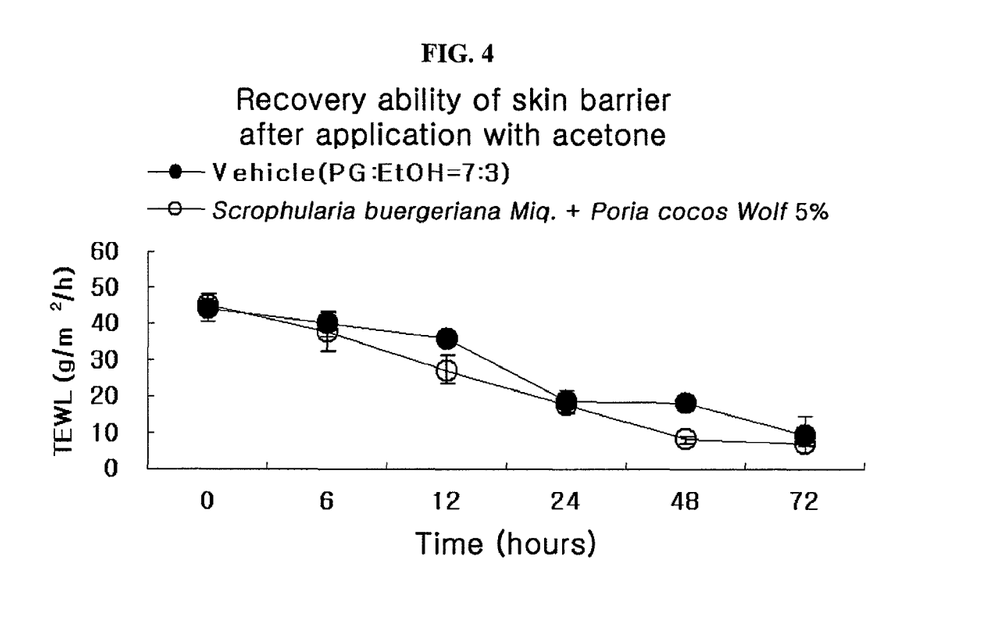
FIG. 4 depicts the recovery ability of the skin barrier of acetone-treated skin following administration of a composition containing an extract of *Scrophularia buergeriana* Miq. and an extract of *Poria cocos* Wolf, in comparison to a vehicle alone control.
Figure 5:
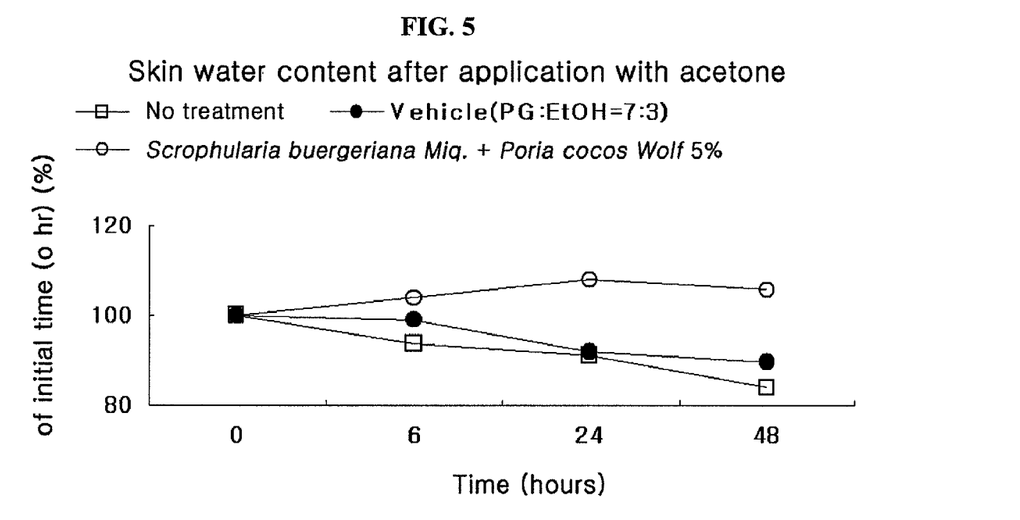
FIG. 5 depicts the skin water content of acetone-treated skin following administration of a composition containing an extract of *Scrophularia buergeriana* Miq. and an extract of *Poria cocos* Wolf, in comparison to a vehicle alone control, or to a no treatment control.

As shown in FIG. 4, in the case of the group treated with the *Scrophularia buergeriana* Miq. extract/*Poria cocos* Wolf extract mixture, the impaired skin barrier function was recovered faster than that of the vehicle group. Also, during the measurement of TEWL, the skin water content was measured with a corneometer (Courage Khazaka, Germany) and, as a result, the skin water content in the group treated with the *Scrophularia buergeriana* Miq. extract/*Poria cocos* Wolf extract mixture was higher than that in the vehicle-treated group. Thus, it could be seen that, in the case of the group treated with the *Scrophularia buergeriana* Miq. extract/*Poria cocos* Wolf extract mixture, the skin water content was increased together with the recovery of impaired skin barrier function. The measurement results are shown in FIG. 5.

TEST EXAMPLE 4

Test of Effect of Inventive Extracts on Increase in Production of Epidermal Lipid (Total Ceramide) on Human Skin In order to evaluate the effects of the *Scrophularia buergeriana* Miq. and *Poria cocos* Wolf extracts on an increase in the synthesis of lipid on the human skin, the following test was carried out. The composition of the test material consisted of 0.5% of Carbopol ETD 2020, 0.45% of TEA 0.45%, 5% test material and the balance of deionized water. On the forearm of each of 12 adult men and women, a region having a size corresponding to the size of a 50-ml polypropylene conical tube was marked, and then 20 μl of each of control groups, the *Scrophularia buergeriana* Miq. extract and the *Scrophularia buergeriana* Miq. extract/*Poria cocos* Wolf extract mixture was applied on the subjects. Herein, the subjects were divided into two groups, lipids were extracted from the subjects at day 3 and day 11 in the following manner, and the extracted lipid were analyzed. Specifically, the forearm was washed with service water, and then subjected to tape stripping one time with Scotch® 810 Magic tape. Then, 1 ml of a mixture of cyclohexane/ethanol (4:1) was added to the forearm using a 50-ml cut polypropylene conical tube as a reservoir and shaken for about 1 minute, and was then transferred into a fresh tube. Then, 1 ml of a mixture of cyclohexane/ethanol (1:1) was added again to the tube and shaken for about 1 minute, and was then transferred into a fresh tube. Then, the content in the tube was dried with nitrogen gas at 50° C. and dissolved and stored in 500 μl of chloroform:methanol=2:1. Each of the samples was dropped onto a silica gel TLC (thin layer chromatography) plate using automated TLC sampler-4 (CAMAG) and was developed with a developing solvent, having the composition ratio shown in Table 4 below, using AMD (automated multiple development).

TABLE 4

| | Chloroform | Methanol | water | Acetic acid | Hexane | Diethyl ether | Petroleum ether | Solvent migration distance (cm) |
|---|---|---|---|---|---|---|---|---|
| First | 40 | 10 | 1 | | | | | 3.0 |
| Second | 190 | 9 | | 1 | | | | 6.5 |
| Third | | | | 2 | 12 | 3 | | 7.5 |
| Fourth | | | | | | | 100 | Top |

After the TLC plate was developed, the size of each band was measured at a wavelength of 570 nm using a TLC Scanner-II densitometer (CAMAG). The production of ceramide in each treated group relative to the production of ceramide in the untreated group taken as 100% is shown in Table 5 and FIG. 6.

TABLE 5

| | Test material (water extract of *Scrophularia buergeriana* Miq.) | 3 days after treatment | 11 days after treatment |
|---|---|---|---|
| Control groups | Untreated group | 100 | 100 |
| | Vehicle | 103 | 98 |
| | Glycerin (5%) | 102 | 94 |
| Groups treated with test group | *Scrophularia buergeriana* Miq. (5%) | 114 | 125 |
| | *Poria cocos* Wolf (5%) | 112 | 121 |
| | *Scrophularia buergeriana* Miq./*Poria cocos* Wolf mixture (5%) | 121 | 134 |

Figure 6:
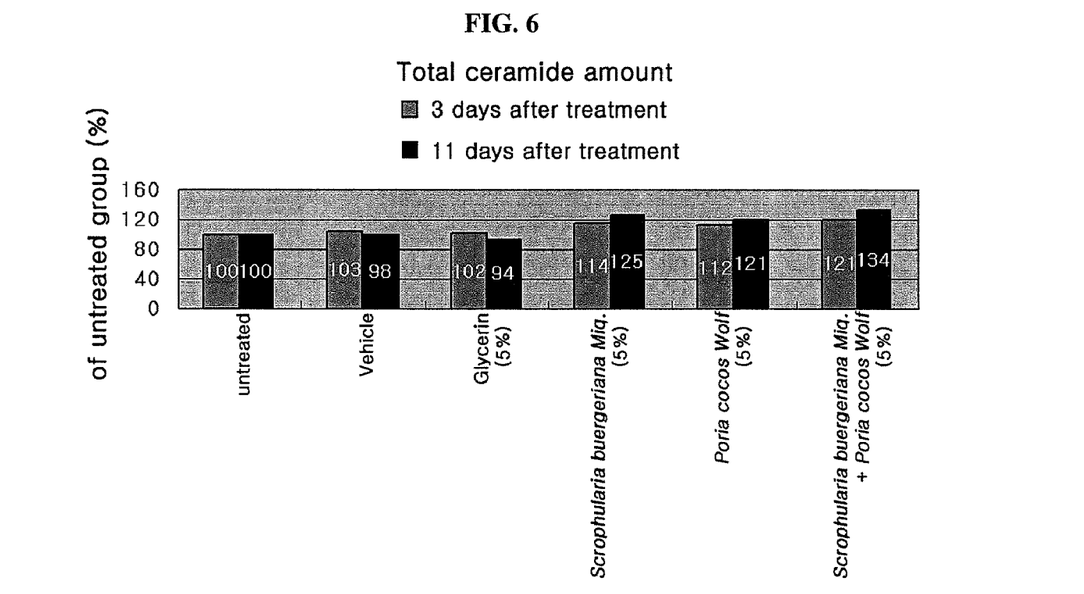
FIG. 6 depicts the total ceramide production in human skin following administration of *Scrophularia buergeriana* Miq. extract alone, *Poria cocos* Wolf extract alone, or a combination of the two extracts, versus untreated, vehicle and glycerin controls.

As shown in Table 5 and FIG. 6, at 3 days and 11 days after treatment, the groups treated with each of the *Scrophularia buergeriana* Miq. extract, the *Poria cocos* Wolf extract and the *Scrophularia buergeriana* Miq. extract/*Poria cocos* Wolf extract mixture showed an increase in the production of ceramide compared to the groups treated with the negative control groups (untreated group/vehicle) and the positive control group (glycerin). This demonstrates that the *Scrophularia buergeriana* Miq. and *Poria cocos* Wolf extracts increased the production of ceramide. Also, it could be seen that the use of the mixture of the *Scrophularia buergeriana* Miq. extract and the *Poria cocos* Wolf extract was more effective than the use of the *Scrophularia buergeriana* Miq. extract alone.

TEST EXAMPLE 5

Test of Activation of PPAR-α (Peroxisome Proliferator Activated Receptor-Alpha) Playing Role in Promotion of Skin Cell Differentiation, Inhibition of Skin Cell Proliferation, Promotion of Lipid Biosynthesis, and Anti-Inflammation Monkey kidney epithelial cell line CV-1 (ATCC CCL 70) was subcultured in a DMEM (Dulbecco's Modified Eagle Medium) containing charcol/dextran-treated 10% fetal bovine serum. A phenol red-free medium was used to avoid the effect of estrogen upon phenol red. As plasmids, used were plasmids having PPRE (PPARs responsive element) as a promoter, followed by firefly luciferase genes as a reporter, the PPRE being activated by PPAR- (gene-containing PPAR- and ligand-bound PPAR-) bound next to the universal promoter expressed under general culture conditions, and a reference plasmid to which renilla luciferase genes were bound.

CV-I cells were plated on a 24-well microtiter plate at a concentration of $5 \times 10^4$ cells per well and cultured for 24 hours. Then, the above three types of plasmid genes were subjected to transient transfection. After 24 hours of culture, the plate was washed with 1×PBS (Phosphate Buffered Saline) and treated with ligand candidates at various concentrations. After 24 hours of further culture, the plate was washed with 1×PBS and the cells were lyzed with 1×PLB (Passive Lysis Buffer) and measured for luciferase activity using the Dual-Luciferase® Reporter Assay System kit.

Figure 7:
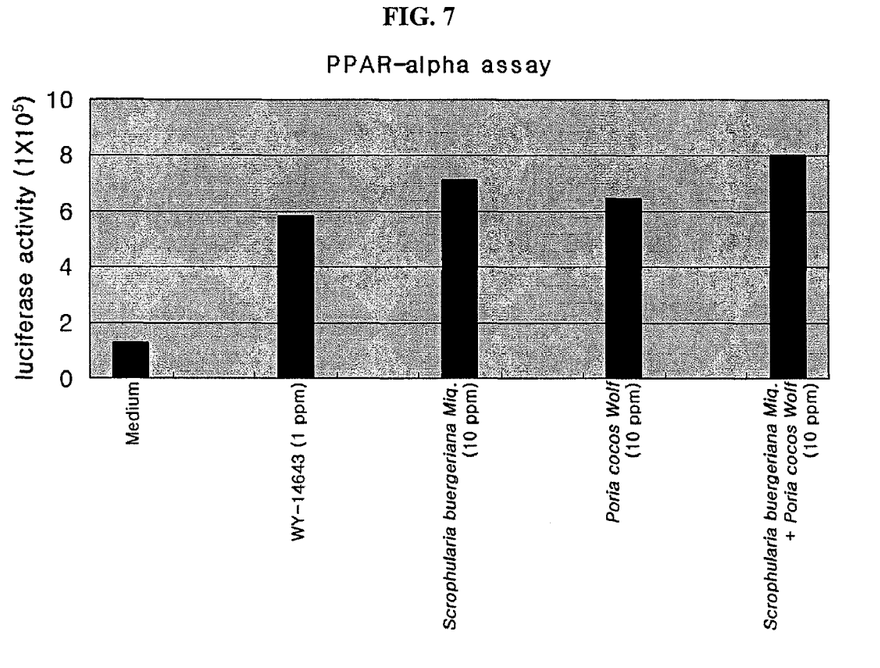
FIG. 7 depicts the activation of Peroxisome Proliferator Activated Receptor-Alpha (PPAR-α) in response to administration of *Scrophularia buergeriana* Miq. extract alone, *Poria cocos* Wolf extract alone, or a combination of the two extracts, versus positive and negative controls.

In this experiment, the positive control was Wy-14,643 which was known to be the most potent PPAR-α ligand, and the negative controls were ethanol, which was used to dissolve the samples, and an untreated group. The results are shown in FIG. 7. As shown in FIG. 7, the use of the mixture of the *Scrophularia buergeriana* Miq. extract and the *Poria cocos* Wolf extract was more effective in activating PPAR-α than the use of the *Scrophularia buergeriana* Miq. extract alone.

From the above results, the *Scrophularia buergeriana* Miq. extract and the *Poria cocos* Wolf extract showed very effects on the promotion of skin cell differentiation, the inhibition of skin cell proliferation, the proliferation of keratinocytes, the recovery of impaired skin barrier function and the increase in skin-moisturizing capacity.

Hereinafter, formulation examples of the inventive composition will be described, but these formulation examples are illustrative only, and the scope of the present invention is not limited thereto.

The herbal medicinal extract in the formulation examples is any one of the extracts of Examples 1 to 3.

FORMULATION EXAMPLE 1

Preparation of Soap

Herbal medicinal extract: 1.00(%)
Oil and fat: suitable amount
Sodium hydroxide: q.s.
Sodium chloride: q.s.
Perfume: small amount
The total amount was made 100% with purified water. Soap was prepared according to the above composition ration.

FORMULATION EXAMPLE 2

Preparation of Lotion

Herbal medicinal extract: 3.00(%)
L-ascorbic acid-2-magnesium phosphate: 1.00
Water soluble collagen (1% aqueous solution): 1.00
Sodium citrate: 0.10
Citric acid: 0.05
Licorice root extract: 0.20
1,3-butylene glycol: 3.00
The total amount was made 100% with purified water. Lotion was prepared according to the above composition ratio (%).

FORMULATION EXAMPLE 3

Preparation of Cream

Herbal medicinal extract: 1.00(%)
Polyethyleneglycol monostearate: 2.00
Self-emulsified glycerin monostearate: 5.00
Cetyl alcohol: 4.00
Squalene: 6.00
Tri-2-glyceryl ethylhexanoate: 6.00
Glycosphingolipid: 1.00
1,3-butylene glycol: 7.00
The total amount was made 100% with purified water. Cream was prepared according to the above composition ratio (%).

FORMULATION EXAMPLE 4

Preparation of Pack

Herbal medicinal extract: 5.00(%)
Polyvinyl alcohol: 13.00
L-ascorbic acid-2-magnesium sulfate: 1.00
Lauroyl hydroxyproline: 1.00
Water-soluble collagen (1% aqueous solution): 2.00
1,3-butylen glycol: 3.00
Ethanol: 5.00
The total amount was made 100% with purified water. Cosmetic pack was prepared according to the above composition ratio (%).

FORMULATION EXAMPLE 5

Preparation of Beauty Solution

Herbal medicinal extract: 2.00(%)
Hydroxyethylene cellulose (2% aqueous solution): 12.00
Xanthan gum (2% aqueous solution): 2.00
1,3-butylene glycol: 6.00
Concentrated glycerin: 4.00
Sodium hyaluronate (1% aqueous solution): 5.00
The total amount was made 100% with purified water. Beauty solution was prepared according to the above composition ratio (%).

INDUSTRIAL APPLICABILITY

As described above, the composition of the present invention can normally restore and maintain the differentiation of skin keratinocytes, and thus can prevent or alleviate dry skin symptoms, atopic symptoms and contact dermatitis, which occur due to incomplete epidermal differentiation.

The invention claimed is:

1. An external composition for skin moisturization, which contains an extract of *Scrophularia buergeriana* Miq. and an extract of *Poria cocos* Wolf, as an active ingredient, wherein the *Scrophularia buergeriana* Miq. extract is contained in an amount of 0.0001-30 wt % based on the total weight of the composition, wherein the extract of *Scrophularia buergeriana* Miq. and the extract of *Poria cocos* Wolf are present in a combination ratio of 1:1, and wherein said composition is in the form of a lotion, cream or gel.

2. The external composition of claim 1, which has an effect of enhancing skin barrier function.

3. The external composition of claim 1, which has an effect of promoting the differentiation of keratinocytes.

4. The external composition of claim 1, which has an effect of promoting the production of ceramide.

5. The external composition of claim 1, which has an effect of activating peroxisome proliferator activated receptor-alpha (PPAR-$\alpha$).

6. The external composition of claim 1, wherein the *Scrophularia buergeriana* Miq extract is prepared by extracting or fractionating *Scrophularia buergeriana* Miq. using a solvent selected from the group consisting of water, ethanol, methanol, hexane, ethyl acetate and butanol.

7. A method for moisturizing skin which comprises applying to a part of skin in need thereof, a composition comprising an extract of *Scrophularia buergeriana* Miq. as an active ingredient, an extract of *Poria cocos* Wolf, and a carrier, wherein the *Scrophularia buergeriana* Miq. extract is contained in an amount of 0.0001-30 wt % based on the total weight of the composition, wherein the extract of *Scrophularia buergeriana* Miq. and the extract of *Poria cocos* Wolf are present in a combination ratio of 1:1, and wherein the administration of said composition to said skin has a synergistic effect on one or more of (a)-(d):

(a) enhancement of skin barrier function;
(b) promotion of keratinocyte differentiation;
(c) promotion of ceramide production; and
(d) activation of peroxisome proliferator activated receptor-alpha (PPAR-$\alpha$).

8. The method of claim 7, wherein the *Scrophularia buergeriana* Miq extract is prepared by extracting or fractionating *Scrophularia buergeriana* Miq. using a solvent selected from the group consisting of water, ethanol, methanol, hexane, ethyl acetate and butanol.

* * * * *